United States Patent [19]

Nakatsu

[11] 4,339,759

[45] Jul. 13, 1982

[54] COLLECTOR CONTROLLER FOR CHROMATOGRAPH

[75] Inventor: Kanji Nakatsu, Kingston, Canada

[73] Assignee: Queen's University at Kingston, Kingston, Canada

[21] Appl. No.: 203,168

[22] Filed: Nov. 3, 1980

[51] Int. Cl.$^3$ .............................................. G01D 9/00
[52] U.S. Cl. .................................. 346/33 R; 141/94; 73/61.1 C
[58] Field of Search ......................... 346/33 R, 33 A; 141/94–96; 73/61.1 C

[56] References Cited

U.S. PATENT DOCUMENTS 3,765,461 10/1973 Keck .............................. 346/33 A X
4,064,512 12/1977 Durrum ............................ 346/33 R Primary Examiner—Joseph W. Hartary
Assistant Examiner—W. J. Brady Attorney, Agent, or Firm—Richard J. Hicks; Stanley E. Johnson

[57] ABSTRACT

An electro-mechanical controller for a fraction collector for a liquid chromatograph in which a conventional strip chart recorder pan holder guide rail is provided with a slider which is pulled along by a contact bar mounted on the pen holder or pushed by the pen holder depending on the direction of travel. The L-bar and pen holder are electrically interconnected to sense the travel of the pen holder and generate an output signal which triggers a timer, the output signal of which fires a one-shot integrated circuit the output signal of which in turn fires a free running timer and time delay circuit to permit time for the solution of the detected peak to travel from the detector to the fraction collector. The output signal from the free running timer and time delay triggers a one-shot IC the output signal of which is fed to an event marker and an integrated circuit inverter controlling the movement of the fraction collector device.

7 Claims, 2 Drawing Figures

COLLECTOR CONTROLLER FOR CHROMATOGRAPH

FIELD OF INVENTION

This invention relates to liquid chromatographs and in particular to the collection of "peak" fractions from a liquid chromatograph column.

BACKGROUND OF THE INVENTION

In the course of study of drug metabolism and the like it is often necessary to collect fractions from a liquid chromatographic column for further analysis by such methods, for metabolites for example, as high resolution mass spectrometry. Less frequently, but nevertheless important, large scale liquid column chromatography is used for purification of drugs synthesized in the laboratory. In many cases the chromatograph peaks corresponding to the fractions which it is desired to collect are not sufficiently separated so that a conventional timed collection of fractions is satisfactory. Resort must be had to fraction collectors which can be made to collect "peaks" when they are connected to a peak detecting device. Many such collectors are available but are generally expensive and because they are electronic in nature are highly susceptible to error due to electrical noise and irregularities in the base-line. Corrections for such errors are both difficult and time consuming.

OBJECT OF THE INVENTION

It is an object of the present invention to provide an inexpensive peak detecting and fraction collecting device which senses the start of a peak and arranges for peak collection and which can accommodate a noisy baseline and correct for a sloping baseline.

Thus by one aspect of the invention there is provided in a liquid chromatographic system which includes a strip chart recorder having a pen holder slidable on a guide rail and a fraction collector, the improvement comprising an electromechanical controller for said collector, comprising:

(a) sensor means including:
  (i) electrically conductive slider means slidably mounted on and electrically insulated from said rail;
  (ii) longitudinally extending bar means mounted on said pen holder and electrically insulated therefrom adapted to draw said slider means along said guide rail in response to movement in one direction of said pen holder including first electrical contact means to contact said slider means and thereby generate a first output signal;
  (iii) second electrical contact means on said pen holder adapted to electrically contact and push said slider along said guide rail in response to movement in the other direction of said pen holder, and thereby generate a second output signal;
(b) integrated circuit timer means arranged to receive said first and second output signals and provide a trigger signal and reset signal in response thereto;
(c) one-shot integrated circuit means arranged to provide a third output signal on receipt of said trigger signal and to reset on receipt of said reset signal;
(d) dual timer integrated circuit means comprising a free running timer which fires at selected time intervals and a delay timer, arranged to receive said third output signal, fire said free running timer and produce a fourth output signal which initiates said delay timer; and
(e) one-shot integrated circuit means arranged to receive a fifth output signal from said delay timer and provide an event marker output signal and a fraction collector movement signal.

DESCRIPTION OF THE DRAWINGS

The invention will be described in more detail hereinafter with reference to the drawings in which.

DETAILED DESCRIPTION

Figure 1:
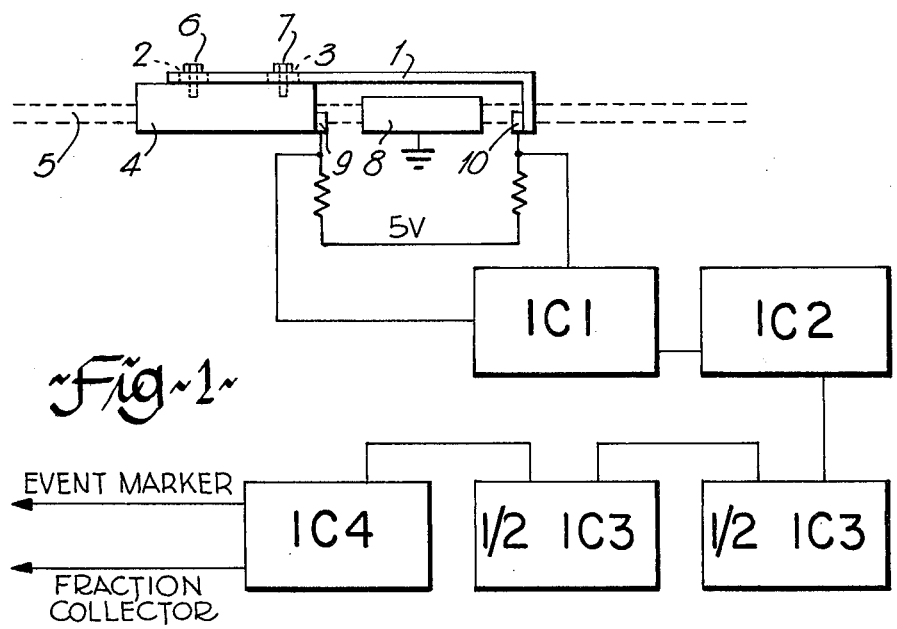
FIG. 1 is a block diagram illustrating the electrical and mechanical aspects of the invention.

As seen in FIG. 1, an L-shaped piece of metal (L-bar) 1 having slots 2,3 adjacent one end thereof is slidably mounted on, and electrically insulated from, a pen holder 4 slidably mounted on a strip chart recorder pen guide rail 5 by means of screws 6,7. Any suitable and conventional strip chart recorder may be employed. A metal slider cylinder 8 mounted on a TEFLON ® bushing, is also slidably mounted on guide rail 5 and electrically grounded. As the pen holder 4 moves from left to right it will push the slider along and make electrical contact therewith via contact 9. As the pen holder 4 moves from right to left, the L-bar 1 pulls the slider along and makes electrical contact therewith via contact 10. The reason for slots 2 and 3 providing adjustable or slidable mounting for L-bar 1 will be discussed in more detail hereinbelow.

Figure 2:
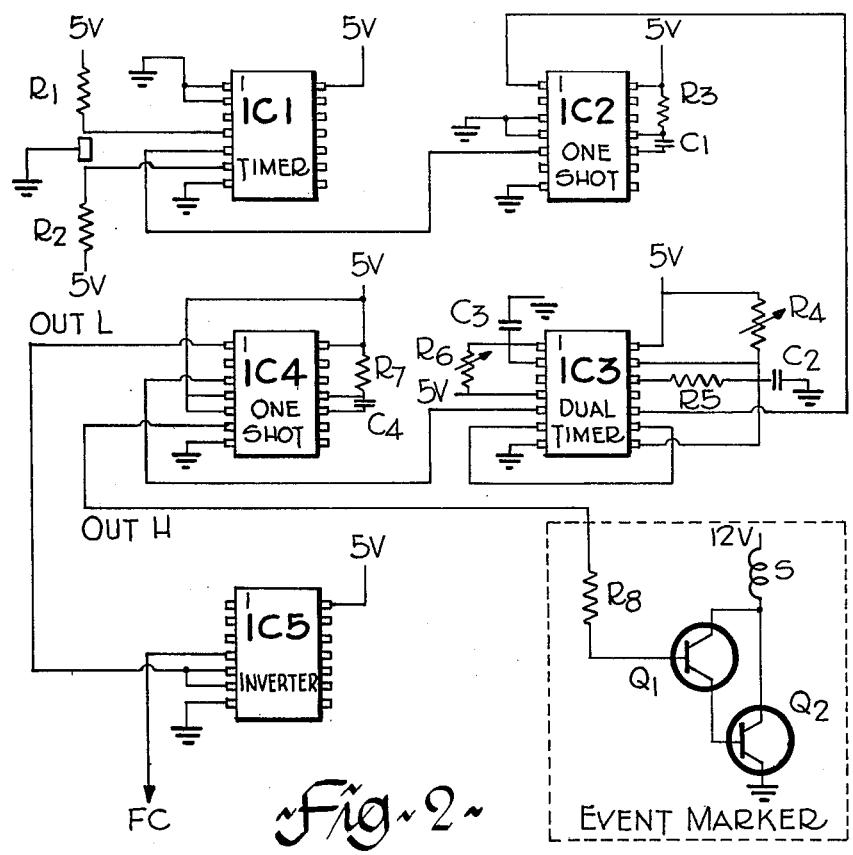
FIG. 2 is a circuit diagram of one embodiment of the invention.

As the pen holder 4 moves from right to left, indicating the commencement of a selected peak, the L-bar contact 10 contacts the slider 8 and triggers the integrated circuit IC1 (half of a 556 dual timer) which fires a one-shot integrated circuit IC2 which is conveniently a 74121 one-shot IC. All integrated circuits (ICs) referred to in this specification are standard ICs which are readily available from national supply houses such as National Semiconductor, Motorola or Fairchild. IC2 cannot then be activated again until after the opposite electrical contact is made when pen holder 4 moves from left to right during the declining phase of the selected peak and the pen holder 4 comes into contact with slider 8 and resets the trigger of the dual timer 556 of integrated circuit IC1. The first half of a dual timer 556 in IC3 contains a free running timer which fires at a preset frequency which can be adjusted by varying the resistance $R_4$ (FIG. 2) (for example, every five minutes) unless it is interrupted. The output from IC2 constitutes such an interruption, causing IC3 to fire when a peak is detected. The output of the first half of IC3 initiates a time delay (for example, 7 seconds) which is contained in the second half of IC3 and which can be varied by adjustment of resistance $R_6$. This delay is required to allow sufficient time for the column effluent from the chromatograph to travel from the detector (not shown) to a suitable fraction collector (not shown). The output from the time delay second half of IC3 fires a one-shot pulse from IC4 which is conveniently a 74121 and is used to drive a recorder event marker and to stepwise advance the fraction collector device to a position ready to receive the next peak fraction.

The output from IC4 (FIGS. 1 and 2) may not be capable of directly driving either the fraction collector or event marker in certain systems, and additional circuitry familiar to those skilled in the art may be required as shown in FIG. 1. For example, a pair of 2N2222 transistors Q1 and Q2 may be used for the event marker and another integrated circuit IC5 (a 7402 inverter) for the fraction collector. The input to the fraction collector is conveniently via the drop counter head so the input line is soldered to the wire which enters the fraction collector to indicate one drop at pin 4 of inverter IC5. The fraction collector may then be set in the drop count mode for one drop. This approach leaves the fraction collector essentially unchanged so that it may also be used in conventional time or drop count modes.

As noted hereinabove L-bar 1 is mounted on pen holder 4 by means of a slotted mounting, so that the operator may readily adjust the spacing between contacts 9 and 10 to alter the amount of pen oscillation permitted without triggering the circuit and thus make allowance for noisy baselines. It will be appreciated also that as long as the slider 8 has not made both reset and trigger contacts, the circuit does not sense a peak thus permitting the baseline to drift in either direction without causing false triggering.

I claim:

1. In a liquid chromatographic system which includes a strip chart recorder having a pen holder slidable on a guide rail and a fraction collector, the improvement comprising an electromechanical controller for said collector, comprising:
  (a) sensor means including:
    (i) electrically conductive slider means slidably mounted on and electrically insulated from said rail;
    (ii) longitudinally extending bar means mounted on said pen holder and electrically insulated therefrom adapted to draw said slider means along said guide rail in response to movement in one direction of said pen holder, including first electrical contact means to contact said slider means and thereby generate a first output signal;
    (iii) second electrical contact means on said pen holder adapted to electrically contact and push said slider along said guide rail in response to movement in the other direction of said pen holder, and thereby generate a second output signal;
  (b) integrated circuit timer means arranged to receive said first and second output signals and provide a trigger signal and reset signal in response thereto;
  (c) one-shot integrated circuit means arranged to provide a third output signal on receipt of said trigger signal and to reset on receipt of said reset signal;
  (d) dual timer integrated circuit means comprising a free running timer which fires at selected time intervals and a delay timer, arranged to receive said third output signal, fire said free running timer and produce a fourth output signal which initiates said delay timer; and
  (e) one-shot integrated circuit means arranged to receive a fifth output signal from said delay timer and provide an event marker output signal and a fraction collector movement signal.

2. The improvement as claimed in claim 1 including
  (f) inverter integrating circuit means arranged to receive said fraction collector movement signal and provide an output signal controlling said fraction collector.

3. The improvement as claimed in claim 1 wherein said sensor means is a peak detector and said first output signal corresponds to a preselected initiation point of a peak.

4. The improvement as claimed in claim 3 wherein said dual timer integrated circuit means includes means to adjust time intervals between firings of said free running timer.

5. The improvement as claimed in claim 4 including means to adjust said delay timer.

6. The improvement as claimed in claim 3 including means to vary the distance between said first and second electrical contact means so as to compensate for electrical noise.

7. The improvement as claimed in claim 6 including slot means in said bar means for adjustable mounting of said bar means on said pen holder.

* * * * *